(12) United States Patent
Hedayat et al.

(10) Patent No.: US 9,134,216 B2
(45) Date of Patent: Sep. 15, 2015

(54) SOOT SENSOR SYSTEM

(75) Inventors: Kayvan Hedayat, Weston, MA (US); John Hart, Lexington, OH (US); Eric Matson, Bellville, OH (US); Mark Wilson, Mansfield, OH (US); Norman Poirier, Raynham, MA (US)

(73) Assignee: Stoneridge, Inc., Warren, OH (US)

( * ) Notice: Subject to any disclaimer, the term of this patent is extended or adjusted under 35 U.S.C. 154(b) by 828 days.

(21) Appl. No.: 13/035,104

(22) Filed: Feb. 25, 2011

(65) Prior Publication Data

US 2011/0203348 A1     Aug. 25, 2011

Related U.S. Application Data

(60) Provisional application No. 61/308,267, filed on Feb. 25, 2010.

(51) Int. Cl.
*G01N 15/06* (2006.01)
*F01N 11/00* (2006.01)

(52) U.S. Cl.
CPC ........ *G01N 15/0656* (2013.01); *F01N 2560/05* (2013.01)

(58) Field of Classification Search
CPC ................. G01N 15/0656; F01N 2560/05
USPC ........... 73/23.31, 23.33, 28.01; 204/424, 426, 204/428, 429; 422/82.01, 82.02
See application file for complete search history.

(56) References Cited

U.S. PATENT DOCUMENTS

| | | | |
|---|---|---|---|
| 4,300,990 A | 11/1981 | Maurer | |
| 4,567,750 A | 2/1986 | Artmann | |
| 4,656,832 A | 4/1987 | Yukihisa et al. | |
| 6,238,536 B1 | 5/2001 | Lundgren et al. | |
| 6,634,210 B1 | 10/2003 | Bosch et al. | |
| 6,833,535 B2 | 12/2004 | Streit et al. | |
| 7,574,895 B2 | 8/2009 | Schnell et al. | |
| 8,035,404 B2 | 10/2011 | Schnell et al. | |
| 2003/0154764 A1 | 8/2003 | Stahl et al. | |
| 2005/0186007 A1* | 8/2005 | Harris et al. | 400/596 |
| 2005/0275497 A1* | 12/2005 | Ramadan et al. | 336/200 |
| 2007/0258186 A1* | 11/2007 | Matyushkin et al. | 361/234 |
| 2008/0190173 A1 | 8/2008 | Wienand et al. | |

(Continued)

FOREIGN PATENT DOCUMENTS

| | | |
|---|---|---|
| GB | 2029028 | 3/1980 |
| JP | S55-106350 | 8/1980 |
| JP | S59-196453 | 11/1984 |
| JP | S59-197847 | 11/1984 |
| JP | S61-186846 | 8/1986 |
| JP | H03-296652 | 12/1991 |
| JP | 2003-166964 | 6/2003 |
| JP | 2009-085959 | 4/2009 |

OTHER PUBLICATIONS

International Search Report and Written Opinion dated Apr. 28, 2011 issued in related International Patent Application No. PCT/US2011/026211.

*Primary Examiner* — Laura Martin
*Assistant Examiner* — Rose M Miller
(74) *Attorney, Agent, or Firm* — Grossman, Tucker, Perreault & Pfleger, PLLC

(57) ABSTRACT

A soot sensor includes a soot sensor including a sensor element and heater element disposed on a first surface of the soot sensor. A soot sensing system may include a soot sensor and circuitry electrically coupled to the sensor and heater elements of the soot sensor. The circuitry is configured to determine an amount of soot accumulated on the soot sensor and to control heating of the heater element in response to the soot accumulation.

20 Claims, 8 Drawing Sheets

(56) References Cited

U.S. PATENT DOCUMENTS

| | | |
|---|---|---|
| 2008/0295575 A1 | 12/2008 | Tokuyasu et al. |
| 2009/0019918 A1 | 1/2009 | Baars et al. |
| 2009/0090622 A1 | 4/2009 | Ripley |
| 2009/0139081 A1 | 6/2009 | Nelson |
| 2009/0217737 A1 | 9/2009 | Dorfmueller et al. |
| 2010/0147052 A1* | 6/2010 | Nelson et al. ............... 73/28.01 |
| 2010/0180669 A1 | 7/2010 | Baars et al. |
| 2011/0314796 A1* | 12/2011 | Nakamura et al. ............. 60/276 |
| 2012/0304736 A1* | 12/2012 | Schmidt et al. ............. 73/23.31 |

* cited by examiner

SOOT SENSOR SYSTEM

CROSS REFERENCE TO RELATED APPLICATIONS

The present application claims the benefit of U.S. Provisional Patent Application Ser. No. 61/308,267, filed Feb. 25, 2010, the entire disclosure of which is incorporated herein by reference.

FIELD

The present disclosure relates generally to a soot sensor, and, more particularly, to a sensor system for detecting soot in an exhaust gas flow.

BACKGROUND

Soot sensors may be used in engine emissions applications, e.g. for on-board diagnostics (OBD). A sensor of this type may be used to detect and measure particulate matter build-up, e.g. soot concentration, in an engine exhaust gas. In diesel engines in particular, it is desirable to have the lowest possible soot particle concentration when exhaust gas is released into the environment. To monitor the operating status of the internal combustion engine, it is expedient for this purpose to position a soot sensor in the exhaust system associated with the internal combustion engine. The soot sensor may be positioned upstream or downstream from a diesel particulate filter (DPF). If it is positioned downstream from the DPF, function monitoring of the DPF may also be performed using the soot sensor. When the (DPF) fails, the soot sensor may detect excessive soot in engine exhaust and alert the vehicle engine control unit (ECU).

Soot sensors may be relatively simple resistive devices. FIG. 1 is a schematic top view of one known configuration of a soot sensor having an on-board heater element, and FIG. 2 is a schematic bottom view of the soot sensor of FIG. 1. The sensor 100 may include a non-conductive substrate 102 defining a first surface 104 and a second surface 106 opposite the first surface 104. A sense element 108 is formed on the first surface 104 of the substrate 102, and includes a conductive material defining a first electrode 110 and a separate second electrode 112. The conductive material may be a precious metal selected to withstand high temperatures, and the first 110 and second 112 electrodes may be electrically separate from each other to establish an open circuit therebetween.

As shown, the first and second electrodes 110, 112 may be configured with inter-digitized "fingers" that maximize a perimeter between the first and second electrodes 110, 112. The first electrode 110 defines a first set of fingers 114 and the second electrode 112 defines a separate second set of fingers 116. In operation, when soot (not shown) from exhaust lands on the sensing element 108, carbon in the soot electrically connects the first and second electrodes 110, 112, effectively lowering the resistance therebetween. The resistance between the electrodes is measured as an indication of the amount of soot present.

FIG. 3 is an enlarged sectional view of the soot sensor of FIGS. 1 and 2 taken along line 3-3. As shown in FIGS. 2 and 3, in some applications, the sensor 100 will also have an on-board heater element 118 implemented on the second surface 106 of the substrate 102. The on-board heater element 118 is configured to heat the soot sensor 100 through resistive heating. For example, it may be desirable to clean off soot that has collected on the first and/or second surfaces 104, 106 of the substrate 102. The on-board heater element 118, which may include a platinum trace with a known resistance, may be activated, heating the sensor element 108 to a relatively high temperature, e.g. 650° C., thereby causing any accumulated soot particles to incinerate.

A soot sensor of the type described above is susceptible to breakdown under the conditions existing in the exhaust system. The electrodes are directly subjected to exhaust gas flow, wherein certain exhaust materials may lead to corrosion of the electrodes and/or contamination of the sensor surface, which may have an interfering effect on soot accumulation measurement. Additionally, the sense element of current soot sensors lacks diagnostic functions capable of sensing a break in the sense element traces. Moreover, on-board heaters included in current soot sensors have difficulty reaching high temperatures required to sufficiently incinerate accumulated soot during high flow conditions.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

DETAILED DESCRIPTION

The present disclosure is generally directed to soot sensors and a soot sensor system for detecting soot particles. In general, a soot sensor system consistent with the present disclosure includes a substrate defining a first surface and a second surface opposing the first surface. A sensor element is formed on the first surface of the substrate. The sensor element includes at least one continuous loop of conductive material disposed on the first surface of the substrate. A heater element is also formed on the first surface of the substrate. The heater element includes at least one continuous loop of conductive material disposed on the first surface of the substrate.

The system may also include first and second electrical contacts disposed at opposite ends of the sensor and heater element loops, respectively. Circuitry is electrically coupled to the first and second pairs of electrodes. The circuitry is configured to determine an amount of soot accumulated on the first surface of the substrate and the sensor element and to control heating of the heater element in response to soot accumulation.

A soot sensor and/or soot sensor system consistent with the present disclosure may be configured to be positioned in an exhaust system of a motor vehicle having a diesel engine. Additionally, a soot sensor and/or soot sensor system may be configured for use in the field of household technology in an oil heating system, for example, it being provided with an appropriately designed support depending on the application. For use in an exhaust system of a motor vehicle, a soot sensor system consistent with the present disclosure may be configured to detect soot accumulation from exhaust gas flow. Additionally, the soot sensor system may be coupled to and configured to communicate with an onboard diagnostics system of a vehicle. Additionally, the soot sensor may be positioned downstream from a diesel particulate filter (DPF) of a motor vehicle having a diesel engine, wherein the sensor may be configured to monitor the performance of the DPF.

Figure 1:
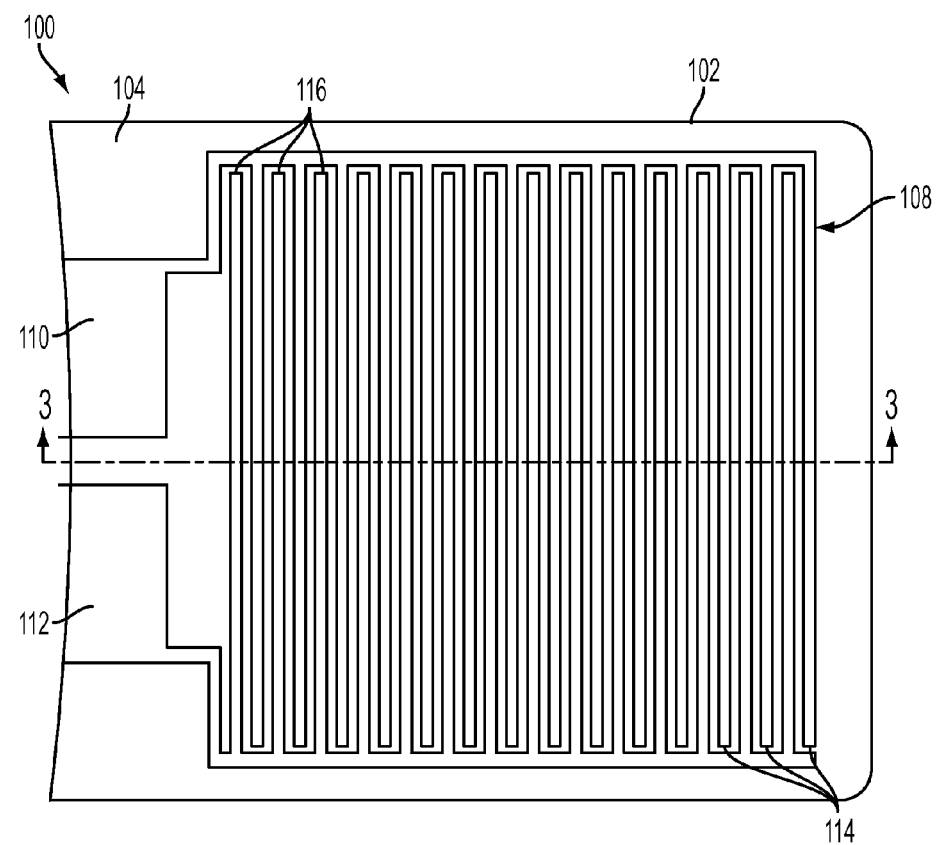
FIG. 1 is a schematic top view of a soot sensor.
Figure 2:
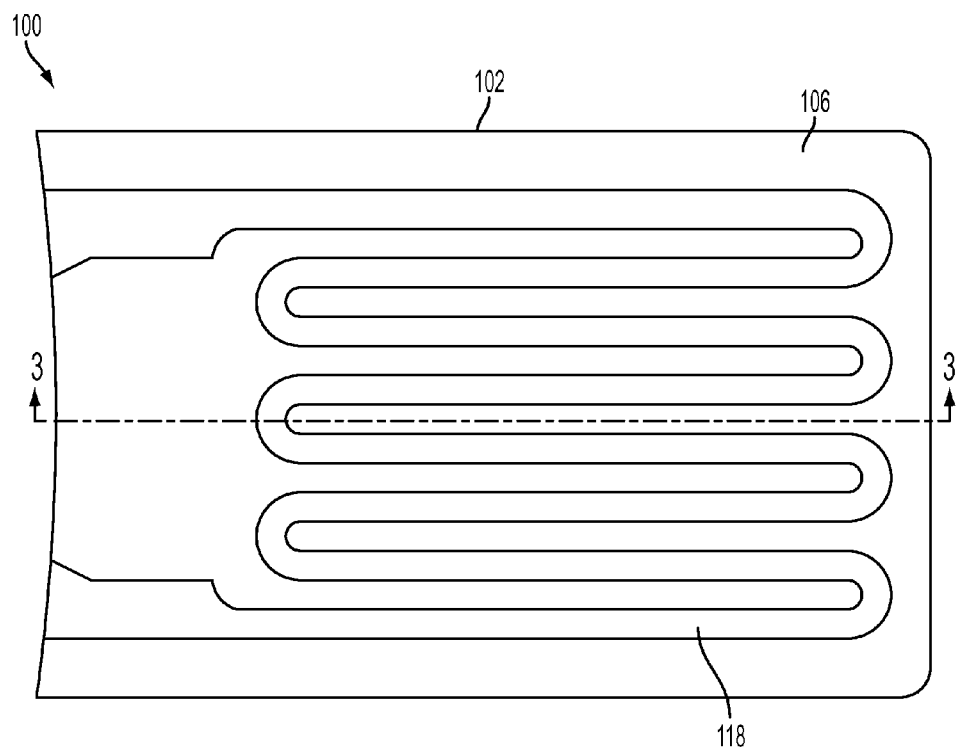
FIG. 2 is a schematic bottom view of the soot sensor of FIG. 1.
Figure 3:
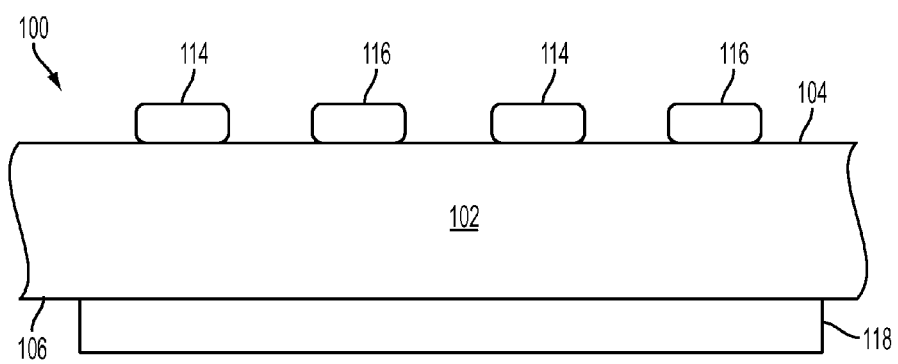
FIG. 3 is an enlarged sectional view of the soot sensor of FIGS. 1 and 2 taken along line 3-3.
Figure 4:
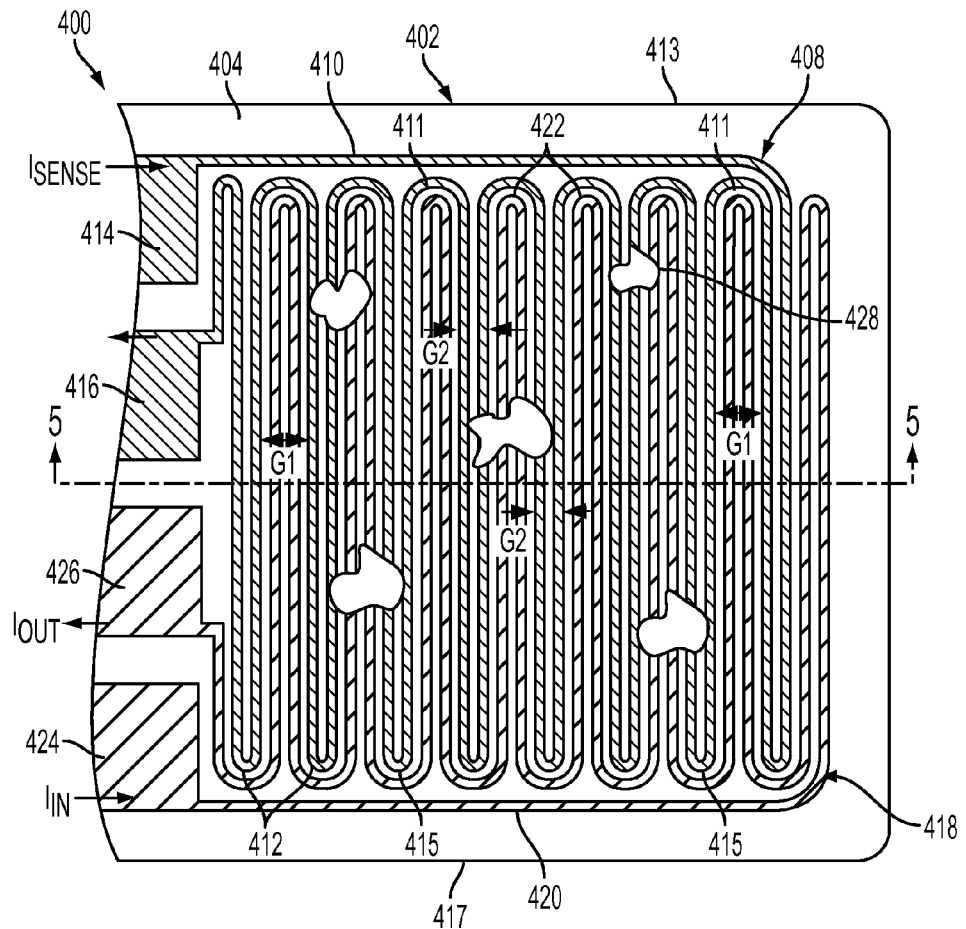
FIG. 4 is a schematic top view of a soot sensor consistent with the present disclosure.
Figure 5A:
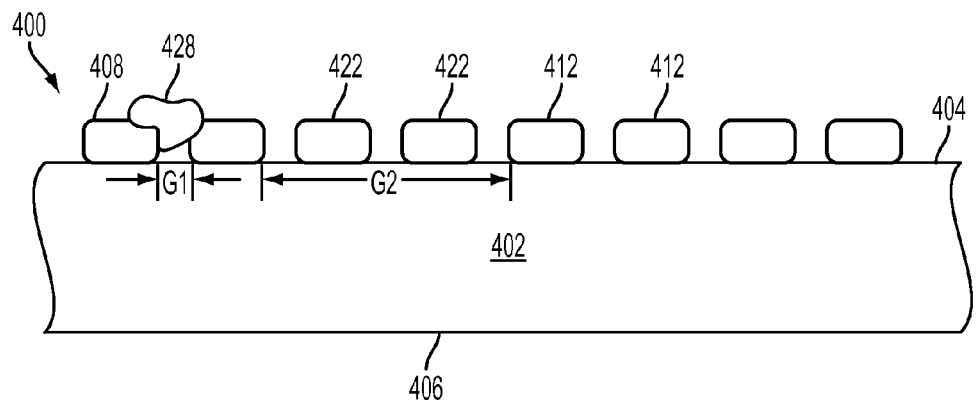
FIG. 5A is a sectional view of a portion of the soot sensor of FIG. 4 taken along line 5-5 consistent with the present disclosure.

Referring to FIG. 4, an embodiment of a soot sensor consistent with the present disclosure is schematically depicted. The soot sensor 400 includes a substrate 402, e.g. constructed from a dielectric or non-conductive material, defining a first surface 404 (e.g. a top surface, as shown in FIG. 5A) and a second surface 406 (e.g. a bottom surface, as shown in FIG. 5A) opposing the first surface 404. The soot sensor 400 includes a sensor element 408 formed on the first surface 404 of the substrate 402. The sensor element 408 includes at least one continuous loop 410 of conductive material disposed on the substrate 402. The loop 410 may take any regular and/or irregular geometric shape, e.g. serpentine, spiral, rectangular, circular, etc.

In the illustrated exemplary embodiment, the loop 410 is arranged in a serpentine configuration including a first set of a plurality of undulations 412 and a plurality of gaps G1 and G2 defined within and between each of the plurality of undulations 412. In the illustrated embodiment, the portions of the loop 410 including turns 411 adjacent the side 413 of the sensor are separated by gaps G1 and the portions of the loop 410 including turns 415 adjacent the side 417 of the sensor are separated by gaps G2, and the gaps G1 are wider than the gaps G2. The term "serpentine" as used herein refers to a configuration including turns of any shape, e.g. arcuate as show in FIG. 4, square, combinations of arcuate and square etc. and also includes turns separated by gaps of uniform and/or differing sizes.

The sensor element 408 further includes first and second electrical contacts 414, 416 at opposite ends of the loop 410. The first and second electrical contacts 414, 416 may be configured for coupling to circuitry for providing current through the loop 410. In the illustrated embodiment, an input current $I_{sense}$ may be provided at the first electrical contact 414 (or second electrical 416 contact).

The value of $I_{sense}$ may be representative of the amount of soot disposed on the sensor 400. In the illustrated embodiment, for example, soot particles 428 are shown as accumulated on the first surface 404 of the substrate 402, including on the sensor element 408. As soot 428 builds up on the sensor element, the resistance of the loop 410 changes, which changes the value of $I_{sense}$. The value of $I_{sense}$ is thus representative of the amount of soot accumulated on the sensor.

The sensor element 400 further include a heater element 418 formed on the first surface 404 of the substrate 402. The heater element 418 includes at least one continuous loop 420 of conductive material disposed on the substrate 402. The loop 420 may take any regular and/or irregular geometric shape, e.g. serpentine, spiral, rectangular, circular, etc, and may be positioned adjacent the sensor element loop 410 in at least a portion of its length.

In the illustrated exemplary embodiment, the loop 420 is arranged in a serpentine configuration including a second set of a plurality of undulations 422 complementary to and interweaving with the first set of plurality of undulations 412. The heater element 418 further includes first and second electrical contacts 424, 426 at opposite ends of the loop 420. The first and second electrical contacts 424, 426 may be configured for coupling to circuitry for providing current through the loop 420. In the illustrated embodiment, an input current $I_{heater}$ may be provided at the first electrical contact 424 (or second electrical 426 contact). In one embodiment, for example, when a threshold amount of soot 428 accumulates on the sensor element 408, e.g. as determined by reaching a threshold value of $I_{sense}$, the heater current $I_{heater}$ may be applied to cause the heater element 418 to heat and at least partially remove, e.g. incinerate, the soot 428, thereby cleaning/regenerating the sensor 400 for continued use.

The sensor element 408 may include electrically conductive materials or metals, such as, gold, platinum, osmium, rhodium, iridium, ruthenium, aluminum, titanium, zirconium, and the like, as well as, oxides, alloys, and combinations including at least one of the foregoing metals. The heater element 418 may include various materials. For example, materials may include platinum, gold, palladium, and the like and/or alloys, oxides, and combinations thereof. The substrate 402 may include a non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication and providing structural integrity and/or physical protection.

FIG. 5A is a sectional view of a portion of the soot sensor 400 of FIG. 4 taken along line 5-5 consistent with one embodiment of the present disclosure. In the illustrated embodiment, soot particles 428 are accumulated on at least the sensor element 408. In particular, when exposed to exhaust gas flow, the soot particles 428 may accumulate within at least one of the plurality of gaps G1 and/or G2 defined within and between each of the plurality of undulations 412 of the loop 410 of the sensor element 408. When the sensor element 408 is free of any soot particles, the electrical circuit of the sensor element 408 created between the first and second electrical contacts 414, 416 has a first resistance. When soot particles 428 accumulate on the sensor element 408, and, in particular, within at least one of the plurality of gaps G1 and/or G2, wherein the soot particle 428 makes contact with the loop 410, the resistance between the first and second electrical contacts 414, 416 may change. Resistance may increase as more soot particles 428 collect and accumulate. The heater element 418 may be activated when it is desired to have accumulated soot particles 428 removed from the soot sensor 408. The heater element 418 may be configured to reach a temperature at which soot particles 428 are incinerated.

Figure 5B:
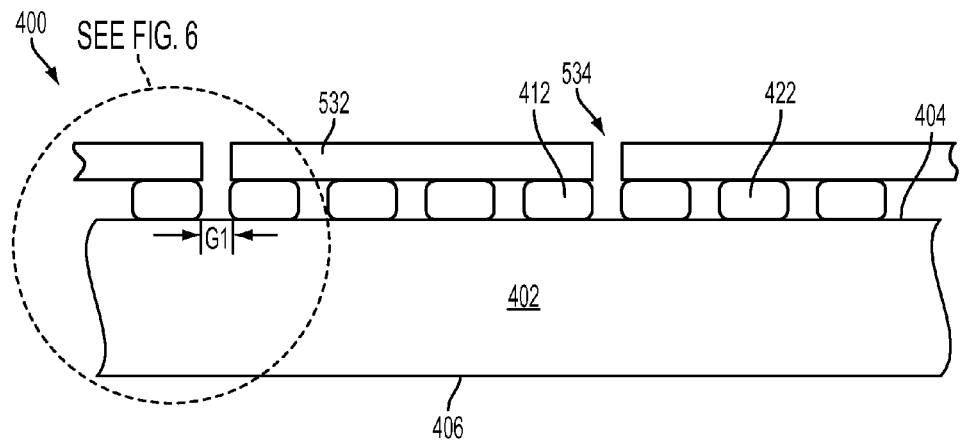
FIG. 5B is a sectional view of a portion of the soot sensor of FIG. 4 taken along line 5-5 according to another embodiment consistent with the present disclosure.
Figure 6:
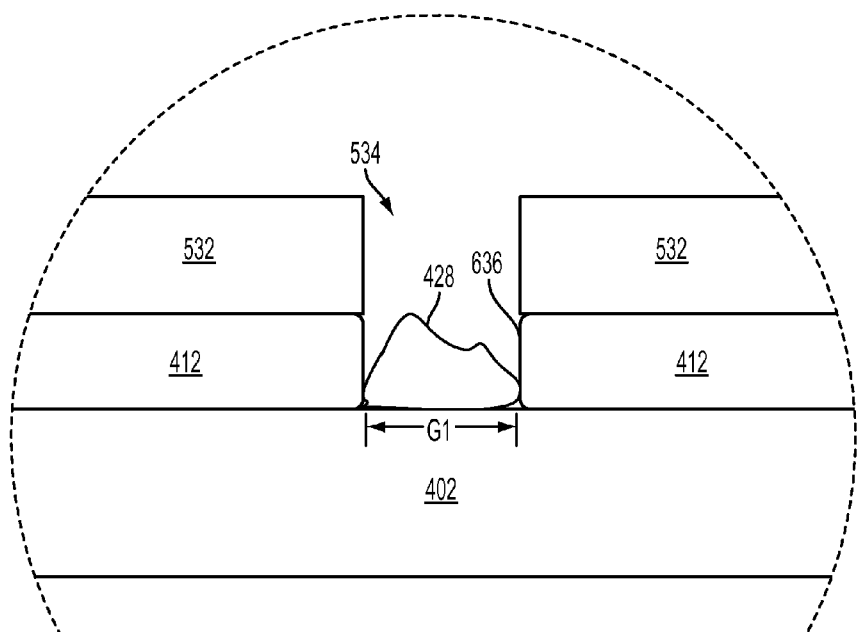
FIG. 6 is an enlarged view of the portion of the soot sensor of FIG. 5B.

FIG. 5B is a sectional view of a portion of the soot sensor of FIG. 4 taken along line 5-5 according to another embodiment consistent with the present disclosure and FIG. 6 is an enlarged view of a portion of the soot sensor of FIG. 5B. In one embodiment, a protective layer 532 is formed over the first surface 404 of the substrate 402 and covers at least a portion of the undulations 412, 422 of the sensor and heater elements 408, 418, respectively. The protective layer 532 may be configured to insulate at least a portion of the undulations 412 of the sensor element 408 from exhaust gas flow. The protective layer 532 further defines a plurality of channels 534 corresponding to and aligned with the plurality of gaps G1 defined by the undulations 412 of sensor element 408.

Referring to FIG. 6, each of the plurality of channels 534 exposes at least a portion of the sensor element, e.g. edges 636 of the undulations 412, to exhaust gas flow and the soot particles 428. In the illustrated embodiment, each of the plurality of channels 534 are sized and/or shaped to allow soot particles 428 to accumulate within at least one of the plurality of channels 534 and the corresponding gap G1, such that soot particles 428 make contact with at least a portion of the exposed sensor element 408 conductive material, e.g. edges 636 of the undulations 412.

Figure 7:
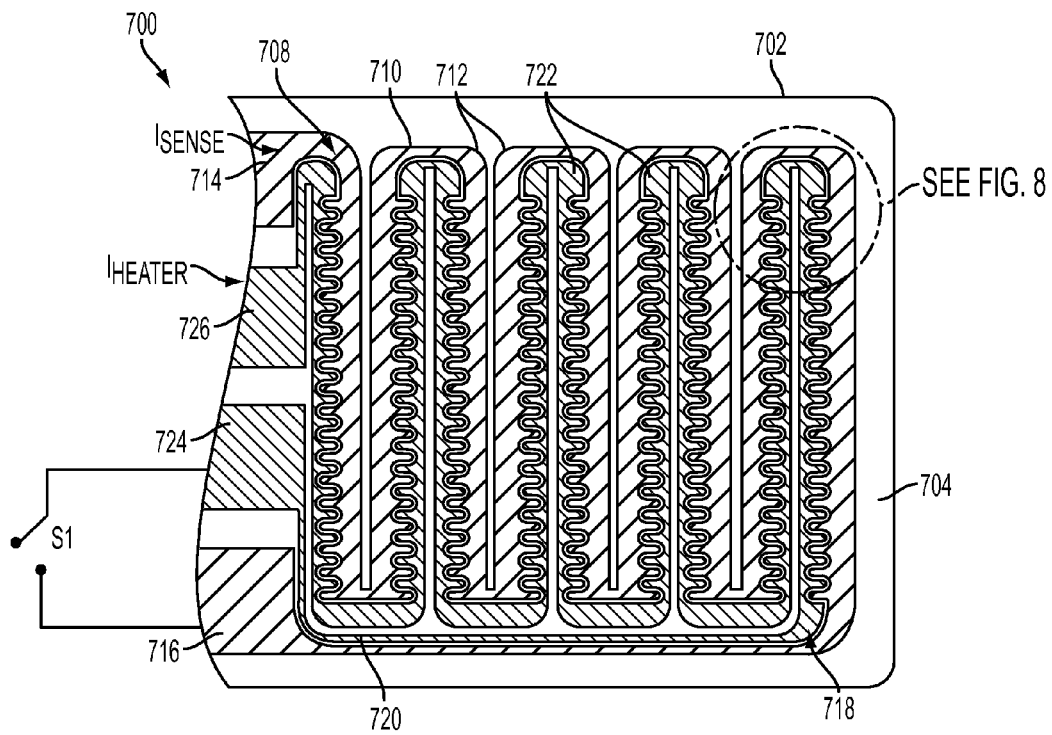
FIG. 7 is a schematic top view of another embodiment of a soot sensor consistent with the present disclosure.
Figure 8A:
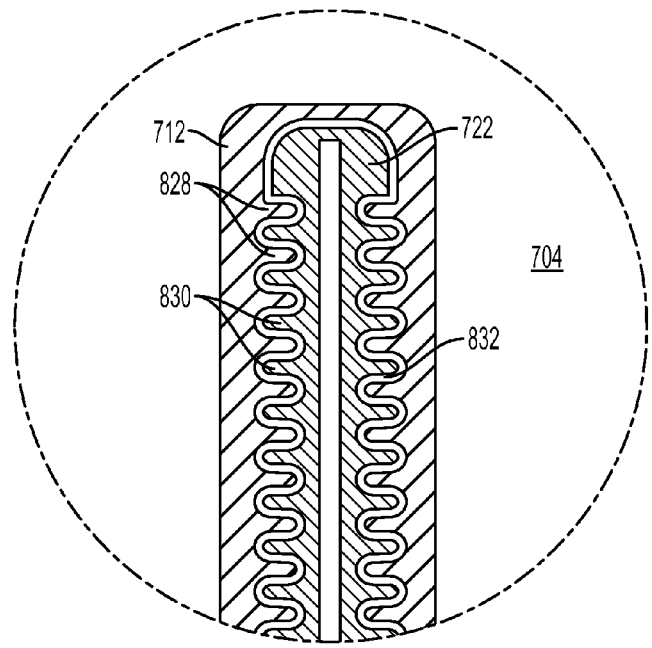
FIG. 8A is an enlarged view of a portion of the soot sensor of FIG. 7.

FIG. 7 is a schematic top view of another embodiment of a soot sensor consistent with the present disclosure. FIG. 8A is an enlarged view of a portion of the soot sensor of FIG. 7. This embodiment is similar to the embodiment of FIG. 4, and like components have been assigned like reference numerals in the seven hundreds rather than the four hundreds. The soot sensor 700 includes a substrate 702 defining a first surface 704. A sensor element 708 and a heater element 718 are formed on the first surface 704. The sensor and heater elements 708, 718 each include at least one continuous loop of conductive material 710, 720, respectively, disposed on the substrate 702. Similar to the embodiment of FIG. 4, the loops 710, 720 may be arranged in a serpentine configuration including first 712 and second 722 sets of undulations. Referring to FIG. 8A, the first 712 and second 722 sets undulations further define first 828 and second 830 subsets of undulations, respectively. A plurality of gaps 832 are defined within and between each of the first 828 and second 830 subsets of plurality of undulations.

The sensor element 708 further includes first 714 and second 716 electrical contacts at opposite ends of the loop 710. The first and second electrical contacts 714, 716 may be configured for coupling to circuitry for providing current through the loop 710. In the illustrated embodiment, an input current $I_{sense}$ may be provided at the first electrical contact 714 (or second electrical 716 contact). Similarly, the heater element 718 further includes first 724 and second 726 electrical contacts at opposite ends of the loop 720. The first and second electrical contacts 724, 726 may be configured for coupling to circuitry for providing current through the loop 720. In the illustrated embodiment, an input current $I_{heater}$ may be provided at the first electrical contact 724 (or second electrical 726 contact).

In the illustrated embodiment, the sensor and heater elements 708, 718 may be configured to be operated separately and independently from one another as described above regarding the embodiment of FIG. 4. Additionally, the soot sensor 700 may further include a switch S1 coupled to the first 724 and second 716 electrical contacts of the heater 718 and sensor 708 elements, respectively, for selectively coupling and decoupling the contacts 724, 716. When the switch S1 is open, the sense current $I_{sense}$ is determined by the resistance of the associated with the loop 710 of conductive material between contacts 714 and 716 and varies with soot particles deposited on the loop 710, thereby allowing the sensor element to sense soot particles. When the switch S1 is closed, loops 710 and 720 are electrically coupled in series establishing a single continuous loop of conductive material between the contacts 714 and 726. The current $I_{sense}$ may then pass through both the sensor 708 and heater 718 elements to allow both the sensor 708 and heater 718 elements to act as a single heater element.

Figure 8B:
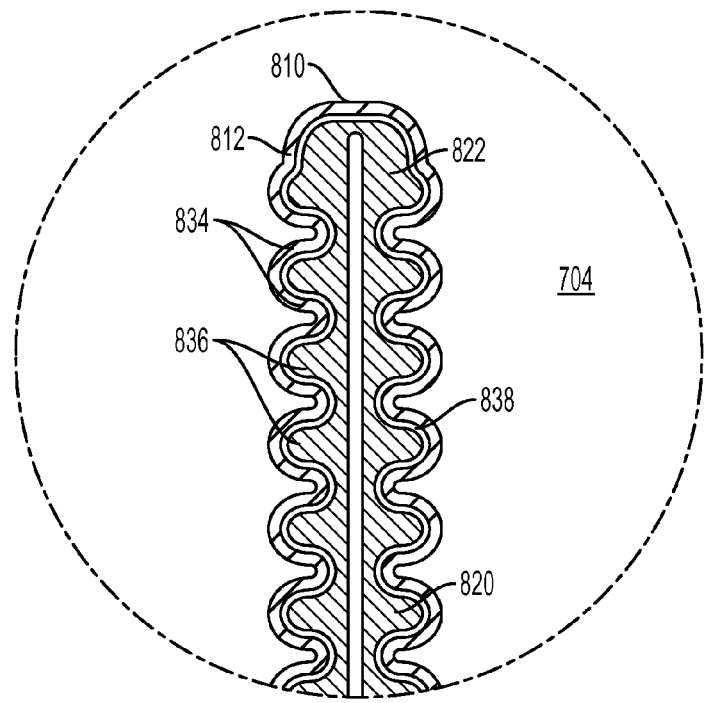
FIG. 8B is an enlarged view of a portion of the soot sensor of FIG. 7 according to another embodiment consistent with the present disclosure.

FIG. 8B is an enlarged view of a portion of the soot sensor of FIG. 7 according to another embodiment consistent with the present disclosure. In the illustrated embodiment, the sensor and heater elements 708, 718 include continuous loops 810, 820 of conductive material disposed on the first surface 704. The loops 810, 820 are arranged in a serpentine configuration including first and second sets of a plurality of undulations 812, 822. The first and second sets of plurality of undulations 812, 822 further define first and second subsets of plurality of undulations 834, 836, respectively. A plurality of gaps 838 are defined within and between each of the first and second subsets of plurality of undulations 834, 836, wherein the gaps 838 are substantially uniform in size and/or shape.

In the illustrated embodiment, the loop 810 is substantially narrower in width than the loop 710 shown in FIG. 8A, thereby increasing the resistance of loop 810 to a value greater than the resistance of loop 710. An increase in resistance may allow the loop 810 to be configured to sense temperature with greater accuracy than the loop 710.

Figure 8C:
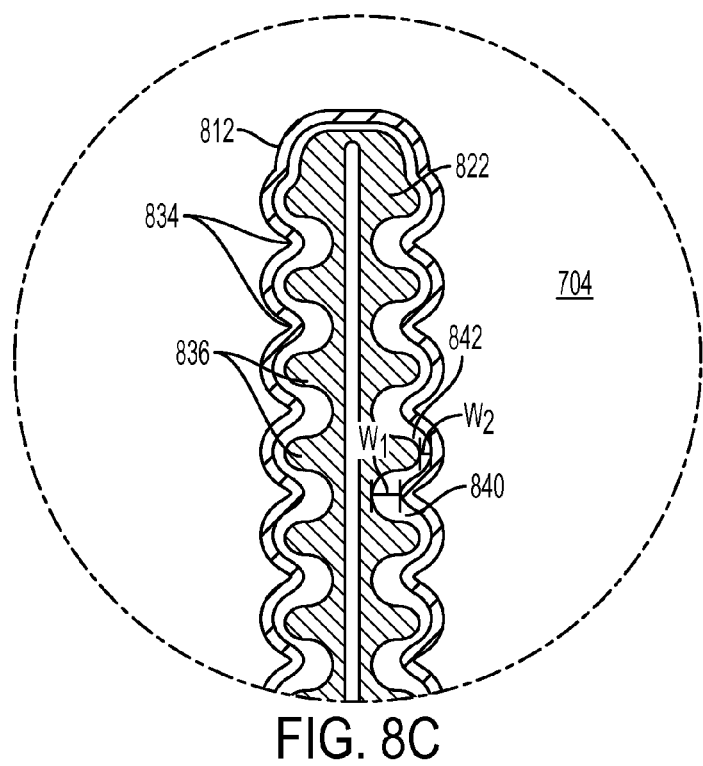
FIG. 8C is an enlarged view of the portion of the soot sensor of FIG. 7 according to another embodiment consistent with the present disclosure.

FIG. 8C is an enlarged view of a portion of the soot sensor of FIG. 7 according to another embodiment consistent with the present disclosure. In the illustrated embodiment, a plurality of gaps 840, 842 are defined within and between each of the first and second subsets of plurality of undulations 834, 836, wherein the gaps 840, 842 vary in size and/or shape. For example, gap 840 has a width $W_1$ and gap 842 has a width $W_2$, wherein width $W_1$ is generally greater than width $W_2$. The gaps 840, 842 of varying size and/or shape may allow the sensor element 708 to have a wider dynamic range of response when sensing soot particle accumulation.

Figure 9:
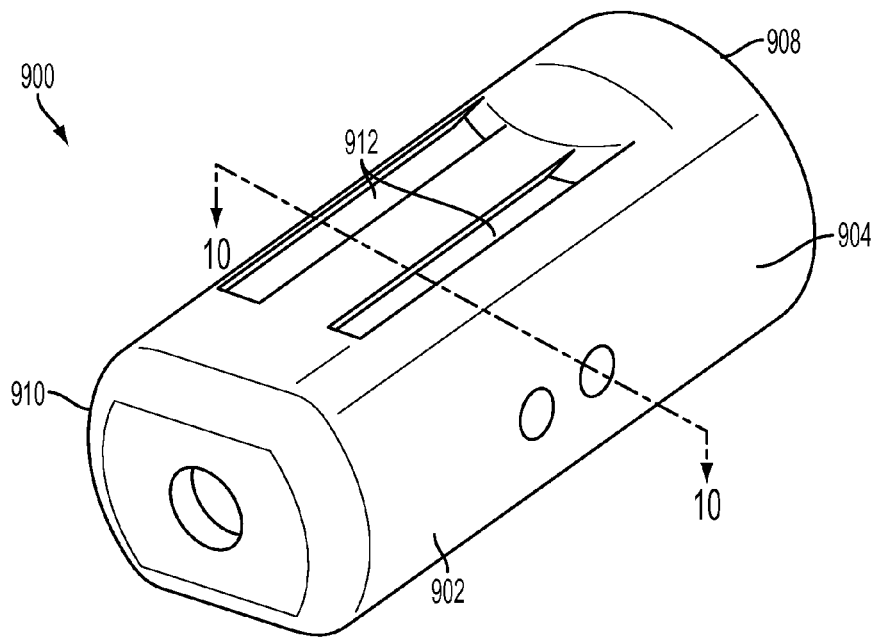
FIG. 9 is perspective view of a soot sensor tip consistent with the present disclosure.
Figure 10:
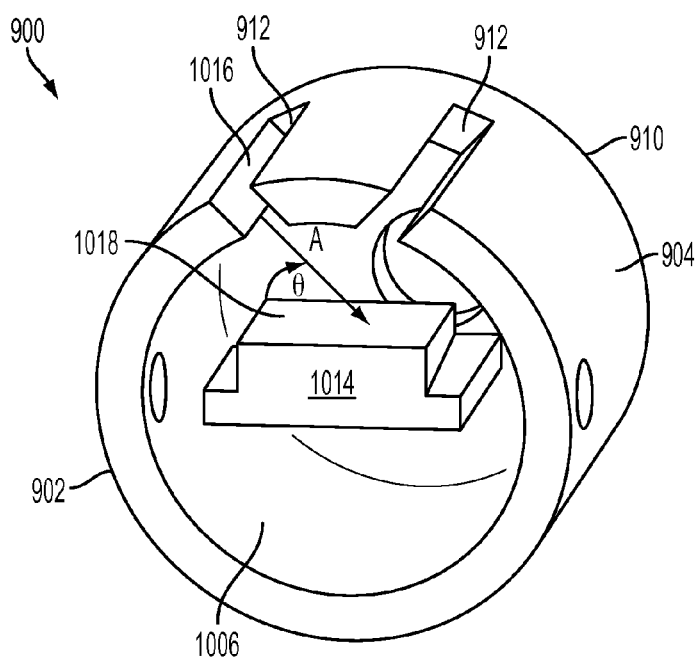
FIG. 10 is an enlarged perspective sectional view of the soot sensor tip of FIG. 9 taken along line 10-10.

FIG. 9 is perspective view of a soot sensor tip consistent with the present disclosure and FIG. 10 is an enlarged perspective sectional view of the soot sensor tip of FIG. 9 taken along line 10-10. The tip 900 is configured to at least partially enclose a soot sensor 1014, wherein the soot sensor 1014 may include embodiments consistent with the present disclosure. The tip 900 includes a body 902 having an exterior surface 904 and an interior surface 1004 and a proximal end 908 and a distal end 910. In the illustrated embodiment, the body 902 gradually transitions from a generally round shape at the proximal end 908 to a generally rectangular shape at the distal end 910. The geometry of the body 902 is configured to minimize volume on the interior of the tip 900. The body 902 defines at least one angularly disposed channel 912 defining a path 1016 from the exterior surface 904 of the body 902 to the interior surface 1006 of the body 902.

The path 1016 is configured to direct exhaust gas flow to the soot sensor 1014, and may be defined by sidewalls oriented at an angle θ of less than 90 degrees relative to the first surface 1018 of the soot sensor 1014, as indicated by the arrow A in FIG. 10. The path 1016 may thus be configured at an angle less than 90 degrees relative to the first surface 1018 to allow soot from exhaust gas flow to enter the interior of the body and impact the soot sensor 1014 at an angle less than 90 degrees relative to the first surface 1018 of the soot sensor 1014. The body 902 may define a plurality of angularly disposed channels 912 positioned along an entire circumference of the body.

Figure 11:
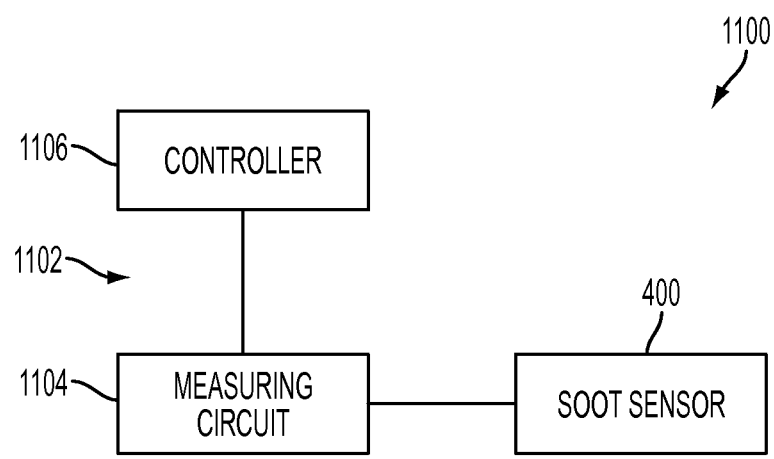
FIG. 11 is a block diagram of one exemplary embodiment of a soot sensor system consistent with the present disclosure.

FIG. 11 is a block diagram of one exemplary embodiment of a soot sensor system consistent with the present disclosure. The soot sensor system 1100 includes a soot sensor 400. For purposes of clarity and description, references will be made to the soot sensor 400 of FIG. 4. It should be noted, however, that the soot sensor system 1100 may include other embodiments of the soot sensor consistent with the present disclosure. The soot sensor system 1100 further includes circuitry 1102 electrically coupled to the soot sensor 400 and configured to provide electrical current to the soot sensor 400. In one embodiment, the circuitry 1102 may be coupled to the first and second electrical contacts 414, 416 and 424, 426 of the sensor and heater elements 408, 418, respectively, for providing currents $I_{sense}$ and/or $I_{heater}$.

The circuitry 1102 includes a measuring circuit 1104 electrically coupled and configured to communicate with a controller 1106. The measuring circuit is also electrically coupled to the soot sensor 400, e.g. to the first and second electrical contacts 414, 416 of the sensor element 408 and/or the first and second electrical contacts 424, 426 of the heater element 418. The measuring circuit 1104 may be configured to apply a voltage between first and second electrical contacts 414, 416 and provide an output to the controller 1106 representative of the resulting value of $I_{sense}$. The controller 1106 may be a known engine control unit (ECU) of an automobile and communication between the soot sensor 440, measuring circuit 1104 and the controller may be accomplished via a known CAN bus.

The value of the current $I_{sense}$ through the sensor element 408 may be utilized to determine an amount of soot that has been deposited on the soot sensor 400, which may be further indicative of an amount of soot in an exhaust stream communicating with the sensor 400. As previously noted, when soot is deposited between the first and second electrical contacts 414, 416 the electrical resistance of the conductive path between the contacts 414, 416 changes, which results in a corresponding change in $I_{sense}$. The value of $I_{sense}$ is representative of the amount of soot that has been deposited on the sensor 400.

The measuring circuit 1104 may also be configured to apply a voltage between the first and second electrical contacts 424, 426 of the heater element. When the value of $I_{sense}$ reaches a predetermined threshold, the controller 1106 may provide an output to the measuring circuit 1104 to cause the measuring circuit to activate the heater element 418 by providing a current $I_{heater}$ to the heater element 418. Upon activation of the heater element 418, the heater element 418 may heat to a temperature at which accumulated soot particles are incinerated, thereby clearing soot particles from the soot sensor 400, particularly the sensor element 408.

Additionally, the circuitry 1102 may be configured to detect open circuits and/or breaks in the sensor and/or heater elements 408, 418. For example, if the sensor element 408 has a break, the circuit between the contacts 414, 416 of the sensor element will be an open circuit or a circuit with higher-than-normal resistance. Thus, if the current $I_{sense}$ falls below a predetermined threshold, the controller 1106 may provide an output indicating failure in the sensor element.

In one aspect, therefore, the present disclosure may feature a soot sensor including a substrate defining a first surface and a second surface opposing the first surface. A sensor element is formed on the first surface of the substrate and includes sensor element loop including at least one continuous loop of conductive material disposed on the first surface. A heater element is also formed on the first surface of the substrate. The heater element includes a heater element loop including at least one continuous loop of conductive material disposed on the first surface.

In another aspect, the present disclosure may feature soot sensor system. The soot sensor system may include a soot sensor including a sensor element and heater element disposed on a first surface of the soot sensor. The soot sensor system may also include circuitry electrically coupled to the sensor and heater elements. The circuitry may be configured to provide electrical current to the sensor element and the heater elements to determine an amount of soot accumulated on the sensor element and to control heating of the heater element in response to the soot accumulated on the sensor element.

In yet another aspect, the present disclosure may feature a method of measuring an amount of soot deposited on a soot sensor. The method may include: providing a soot sensor consistent with the present disclosure; monitoring a sense current through the sensor element, the current being representative of an amount of soot accumulated on the sensor element; and providing heater current through the heater element in response to the monitoring step when the sense current reaches a predetermined threshold to thereby remove at least a portion of the soot accumulated on the sensor element While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

What is claimed is:

1. A soot sensor system comprising:
a soot sensor comprising:
a substrate defining a first surface and a second surface opposing said first surface; and
a first and at least a second continuous loop of conductive material disposed on said first surface, said first continuous loop comprising a first set of a plurality of intertwined sections, and said second continuous loop comprising a second set of a plurality of intertwined sections, each of said first and said second set of said plurality of intertwined sections further defining a first and a second subset of intertwined sections, respectively, interweaving with each other;
wherein a sense current between said first and said second continuous loops of conductive material is representative of soot in contact therewith; and
wherein said first and said second continuous loops of conductive material are configured to at least partially incinerate soot contacting said soot sensor.

2. The soot sensor system of claim 1 wherein said first and said second continuous loops each comprises first and second electrical contacts at opposite ends thereof.

3. The soot sensor system of claim 1, wherein said first and said second continuous loops are disposed between a protective layer and said first surface of said substrate, and wherein said protective layer defines a plurality of channels corresponding to and aligned with a plurality of gaps of said first continuous loop such that portions of said conductive material of said first continuous loop are exposed to exhaust gas flow and soot particles therefrom.

4. The soot sensor of claim 1, said soot sensor further comprising a switch configure to connect said first continuous loop and said second continuous loop.

5. The soot sensor system of claim 4, wherein said switch is configured to connect said first continuous loop and said second continuous loop in series.

6. The soot sensor system of claim 1 further comprising a tip configured to at least partially enclose said soot sensor, said tip comprising a body, a proximal end, and a distal end, said body transitioning from a generally round shape at said proximal end to a generally rectangular shape at said distal end.

7. The soot sensor system of claim 1 further comprising a tip configured to at least partially enclose said soot sensor, said tip comprising a body having an exterior surface and an interior surface, said body defining at least one angularly disposed channel defining a path from said exterior surface of said body to said interior surface of said body, said path configured to direct exhaust gas flow to said soot sensor.

8. The soot sensor system claim 7 wherein said path is configured at an angle relative to said first surface of less than 90 degrees.

9. The soot sensor system claim 1, further comprising a controller electrically coupled to said first and said second continuous loops, said circuitry configured to detect an open circuit of at least one of said first or said second continuous loops based on a diagnostics sense current applied to said at least one of said first or said second continuous loops.

10. The soot sensor of claim 1, wherein said first and said second set of said plurality of intertwined sections comprises a first and a second plurality of undulations, respectively, and wherein said first and said second subset of intertwined sections comprises a first and a second subset of undulations, respectively.

11. A soot sensor system comprising:
a soot sensor comprising:
a substrate defining a first surface and a second surface opposing said first surface;
a first and at least a second continuous loop of conductive material disposed on said first surface; and
a controller coupled to said first and said second continuous loops, said controller configured to:
cause a sense current to be applied to at least one of said first and said second continuous loops to detect soot accumulated on said soot sensor;
cause a heater current to be applied to at least one of said first or said second continuous loops to control heating of said soot sensor in response to said soot accumulated on said soot sensor; and
detect an open circuit of at least one of said first or said second continuous loops based on a diagnostics sense current applied to said at least one of said first or said second continuous loops.

12. The soot sensor system of claim 11 wherein said first continuous loop comprises a first set of a plurality of intertwined sections, and wherein said second continuous loop comprises a second set of a plurality of intertwined sections, said first and said second set of said plurality of intertwined sections further defining a first and a second subset of intertwined sections, respectively, interweaving with each other.

13. The soot sensor system of claim 11, wherein said first and said second continuous loops are disposed between a protective layer and said first surface of said substrate, and wherein said protective layer defines a plurality of channels corresponding to and aligned with a plurality of gaps of said first continuous loop such that portions of said conductive material of said first continuous loop are exposed to exhaust gas flow and soot particles therefrom.

14. The soot sensor system of claim 11 further comprising a switch configure to connect said first continuous loop and said second continuous loop.

15. The soot sensor system of claim 11 further comprising a tip configured to at least partially enclose said soot sensor, said tip comprising a body, a proximal end, and a distal end, said body transitioning from a generally round shape at said proximal end to a generally rectangular shape at said distal end.

16. The soot sensor system of claim 11 further comprising a tip configured to at least partially enclose said soot sensor, said tip comprising a body having an exterior surface and an interior surface, said body defining at least one angularly disposed channel defining a path from said exterior surface of said body to said interior surface of said body, said path configured to direct exhaust gas flow to said soot sensor.

17. The soot sensor system of claim 16 wherein said path is configured at an angle relative to said first surface of less than 90 degrees.

18. The soot sensor system of claim 11 wherein said circuitry is configured activate at least one of said first and said second continuous loops when said soot accumulated on said soot sensor reaches a predetermined threshold level to heat to a temperature at which removes at least a portion of said soot accumulated on said soot sensor.

19. The soot sensor system of claim 11, wherein said controller is configured to provide an output indicating a failure in said at least one said first or second continuous loops based on a comparison of said diagnostics current with a predetermined threshold.

20. A method of operating a soot sensor comprising a first and at least a second continuous loop of conductive material disposed on a first surface of a substrate, said method comprising:
- monitoring a sense current between said at least one of said first and said second continuous loops to detect soot accumulated on said soot sensor;
- providing heater current to at least one of said first and said second continuous loops in response to said monitoring step when said sense current reaches a predetermined threshold to thereby remove at least a portion of said soot accumulated on said soot sensor; and
- detecting an open circuit of at least one of said first or said second continuous loops based on a diagnostics sense current applied to said at least one of said first or said second continuous loops.

* * * * *